United States Patent [19]
Flohr et al.

[11] Patent Number: 5,577,501
[45] Date of Patent: Nov. 26, 1996

[54] COMPUTED TOMOGRAPHY APPARATUS WITH COMPENSATION FOR SMOOTHING WHICH OCCURS IN INTERPOLATION OF DATA

[75] Inventors: Thomas Flohr, Uehlfeld; Heinrich Wallschlaeger, Erlangen, both of Germany

[73] Assignee: Siemens Aktiengesellschaft, Munich, Germany

[21] Appl. No.: 313,388

[22] Filed: Sep. 27, 1994

[30] Foreign Application Priority Data

Oct. 13, 1993 [DE] Germany ............. 43 34 937.4

[51] Int. Cl.⁶ ............................................. A61B 5/05
[52] U.S. Cl. ........................ 128/653.1; 378/4; 382/131
[58] Field of Search ................ 128/653.1; 364/413.14, 364/413.15, 413.16, 413.18, 413.19, 413.20, 413.21; 378/4, 21, 62; 382/42, 43, 44, 45, 128, 131

[56] References Cited

U.S. PATENT DOCUMENTS

| 4,135,247 | 1/1979 | Gordon et al. | 364/413.16 |
|---|---|---|---|
| 4,580,219 | 4/1986 | Pelc et al. | 364/413.21 |
| 4,583,241 | 4/1986 | Walters | 378/19 |
| 5,307,264 | 4/1994 | Waggener et al. | 364/413.21 |
| 5,446,799 | 8/1995 | Tuy | 364/413.17 |

OTHER PUBLICATIONS

"Die Fouriertransformation in der Bildverarbeitung 1. Teil," Müller, Elektronik 3/2.2 (1990), pp. 50–59.
"Reordering Schemes for Multiple–Rotation Fan–Beam CT Scanner," Jelinek et al., IEEE Trans. on Med. Imag., vol. MI-4, No. 4, Dec. 1985, pp. 215–221.

*Primary Examiner*—Marvin M. Lateef
*Assistant Examiner*—Brian L. Casler
*Attorney, Agent, or Firm*—Hill, Steadman & Simpson

[57] ABSTRACT

In a computed tomography apparatus wherein an examination subject is irradiated by an x-ray beam from a number of different angular positions, a measured data set is obtained in a first geometry, and the reconstruction of the tomographic image ensues by interpolation of the measured data in a second geometry. The interpolation results in an unwanted smoothing of the data. In order to compensate for this smoothing, the data in the frequency space are divided by the average Fourier transform of the interpolation function, or alternatively, a discrete convolution of the data in the spatial domain is undertaken.

3 Claims, 2 Drawing Sheets

COMPUTED TOMOGRAPHY APPARATUS WITH COMPENSATION FOR SMOOTHING WHICH OCCURS IN INTERPOLATION OF DATA

BACKGROUND OF THE INVENTION

1. Field of the Invention

The present invention is directed to compensating for smoothing which occurs in the interpolation of data arising in the conversion of data from a first geometry to a second geometry, and specifically to a computed tomography apparatus with such compensation.

2. Description of the Prior Art

The attenuation values of x-rays are measured in a plurality of directions in computed tomography in order to calculate cross sectional images of a specific subject. This measurement is based on a geometry, for example that of a fan beam system or of a parallel beam system. The desired computer tomograms are acquired by a reconstruction algorithm which is in turn based on a certain geometry. When one wishes to work with a different geometry in the image reconstruction than was used in the measurement (data acquisition), then the measured attenuation values (data) must be correspondingly converted before the reconstruction. This occurs by interpolation.

A problem arises in deriving data $P_{k,l}$ in a different raster $\alpha_{k,l}=(1-\tilde{\delta}_k)\Delta\theta$ with $l=-M, \ldots, M$ from data $F_n$ in a raster $\alpha_n=n\Delta\alpha$ with $n=-M, \ldots, M$. The value $\tilde{\delta}_k$ is composed of a whole-number part $\delta'_k=\text{int}(\tilde{\delta}_k)$ and a fractional part $\epsilon_k=\tilde{\delta}_k-\delta'_k$. This conversion thus occurs from one raster to a different raster having a different sampling interval and a different raster position by an interpolation $h(\alpha)$ according to the relationship $$P_{k,l} = \sum_{n=-M}^{M} h(\alpha_{k,l}-\alpha_n) F_n \tag{1}$$

For explanatory purposes, the conversion onto a raster $\alpha_{k,l}=(1-\tilde{\delta}_k)\Delta\alpha$ with the linear interpolation $$h(\alpha) = \begin{bmatrix} 1 - \left|\dfrac{\alpha}{\Delta\alpha}\right| & \text{for} \quad |\alpha| < \Delta\alpha \\ 0 & \text{otherwise} \end{bmatrix} \tag{2}$$

shall be considered below. The exemplary conversion thus occurs from a first raster to another raster having the same sampling interval, but having a different scanning raster position.

A problem is that such interpolations lead to a smoothing of the data. This is expressed in a reduction of specific frequencies in the spectrum of the interpolated data $P_{k,l}$ dependant on the properties of the type of interpolation employed.

SUMMARY OF THE INVENTION

It is an object of the present invention to provide a computed tomography apparatus wherein the smoothing of data which arises in the interpolations necessitated by converting the data from a first geometry into a second geometry are compensated.

The above object is achieved in a first embodiment of the invention wherein data corresponding to x-rays attenuated by an examination subject irradiated from a number of different angular positions are acquired in a first geometry, with image reconstruction ensuing by interpolation of the measured data into a second geometry, with compensation for smoothing which arises as a result of the interpolation being accomplished by dividing the data in the frequency space by the average Fourier transform of the interpolation.

The above object is also achieved in a second embodiment of the invention wherein measured data are again obtained using a first geometry and image reconstruction ensues by interpolation of the measured data in a second geometry, and wherein smoothing which arises as a result of the interpolation is compensated by a discrete convolution of the data in the spatial domain. In this second embodiment, the convolution in the locus space can be combined with the interpolation.

DESCRIPTION OF THE PREFERRED EMBODIMENTS

Figure 1:
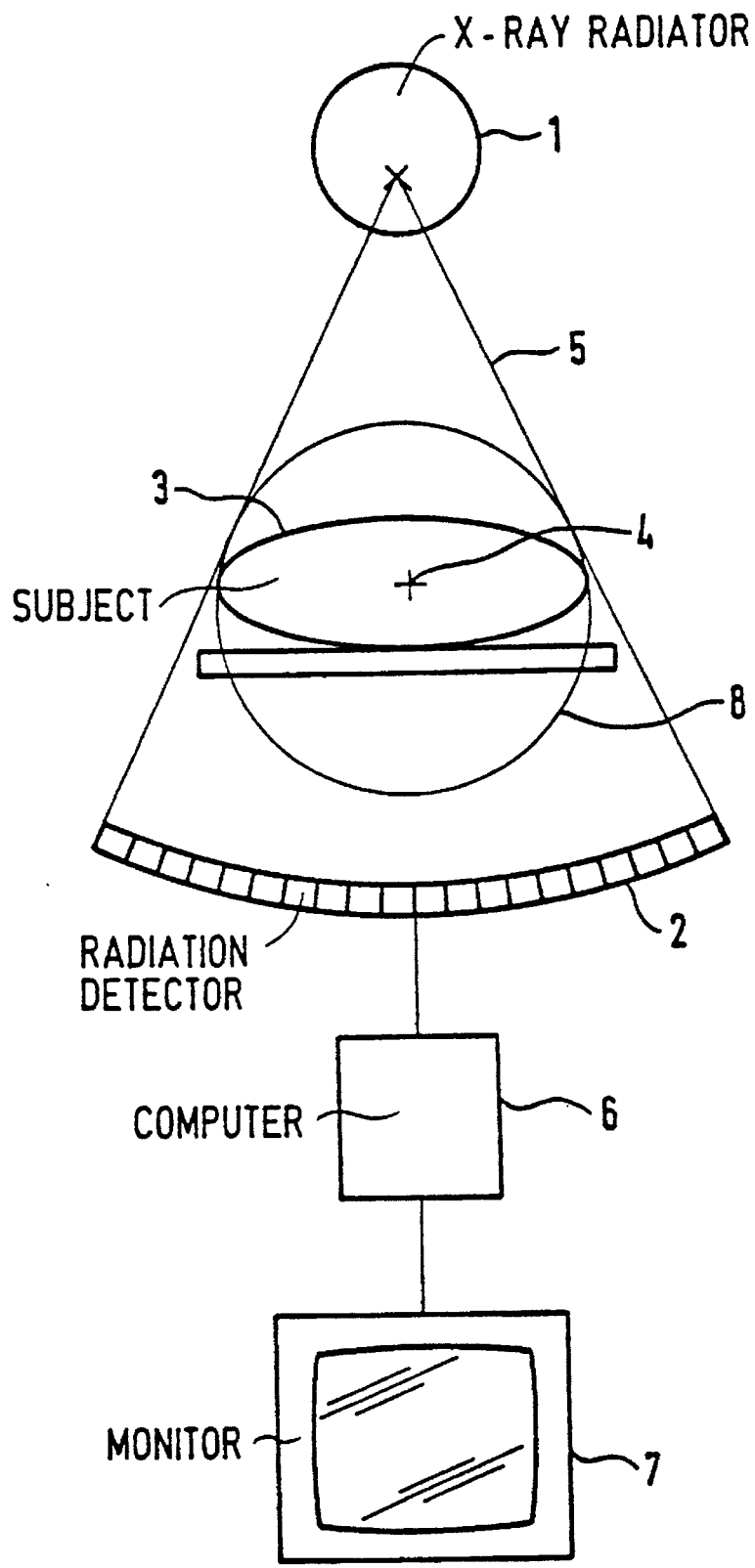
FIG. 1 is a schematic illustration showing the basic components of computed tomography apparatus operating in accordance with the principles of the present invention.

FIG. 1 shows a computed tomography apparatus having an x-ray radiator 1 and a radiation detector 2 composed of a row of detector elements. The x-ray radiator 1 and the radiation detector 2 are rotated around a system axis 4 for scanning a subject 3, so that the subject 3 is trans-irradiated by a fan-shaped x-ray fan beam 5 emanating from the x-ray radiator 1 from different directions. The data supplied by the detector elements of the detector 2 are supplied to a computer 6 that reconstructs tomograms of the subject 3 that are reproduced on a monitor 7. The subject 3 lies in a measuring field 8 covered by the x-ray beam 5.

The computed tomography apparatus according to FIG. 1 is based on the fact that the data supplied by the detector 2 are present in a first geometry and that the image reconstruction in the computer 6 ensues by interpolation in a second geometry.

For a fixed value k, the interpolation $h(\alpha)$ corresponds to a specific Fourier transform $\hat{h}_k(\rho)$. It is dependent on the scanning raster position of $\alpha_{k,l}$. In the example of the linear interpolation, this results in $$\hat{h}_k(p)=\epsilon_k\exp(2\pi ip(1-\epsilon_k)\Delta\alpha)+(1-\epsilon_k)\exp(-2\pi ip\epsilon_k\Delta\alpha) \tag{3}$$

$$= \begin{bmatrix} 1 & \text{for} \quad \epsilon_k=0 \\ \cos\pi\rho\Delta\alpha & \text{for} \quad \epsilon_k=0.5 \end{bmatrix} \tag{4}$$

It can now be shown that an effect of the interpolation averaged over all raster positions $0\leq\epsilon_k<1$ corresponds to a Fourier transform $\hat{h}_M(\rho)$ that results from an arbitrarily fine scanning of $h(\alpha)$. In the example, this is $$\hat{h}_m(\rho)=\Delta\alpha\,\text{sinc}^2(\pi\rho\Delta\alpha). \tag{5}$$

The higher frequencies in the spectrum $\hat{P}_k(\rho)$ of $P_{k,l}$ are thus attenuated on average according to $\hat{h}_M(\rho)$, this effecting a smoothing.

A compensation of this smoothing ensues according to a first embodiment of the invention wherein the data in the frequency space are divided by the average Fourier transform of the interpolation.

$$\tilde{\hat{P}}_k(\rho) = \frac{\Delta\alpha}{\hat{h}_M(\rho)} \hat{P}_k(\rho); \quad (6)$$

for example, $$\tilde{\hat{P}}_k(\rho) = \frac{1}{\mathrm{sinc}^2(\pi\rho\Delta\alpha)} \hat{P}_k(\rho). \quad (7)$$

For the practical case wherein one does not have a continuous spectrum but instead has a discrete spectrum at the frequencies $\rho_q = q/(2M\Delta\theta)$, $q=-M, \ldots M$, equation (6) becomes $$\tilde{\hat{P}}_{k,q} = \frac{\Delta\alpha}{\hat{h}_M(\rho_q)} \hat{P}_{k,q}, \quad (8)$$

in the example, thus, $$\tilde{\hat{P}}_{k,q} = \frac{1}{\mathrm{sinc}^2(\pi\rho_q\Delta\alpha)} \hat{P}_{k,q} \quad (9)$$

It is useful for some applications to replace this product in the frequency space by a convolution in the spatial domain. When equation (8) is approximated by a short, discrete convolution $$\tilde{P}_{k,l} = \sum_{j=-J}^{J} a_j P_{k,l+j} \quad (10)$$

in the spatial domain, then one can begin with the smoothing compensation before all data $P_{k,l}$ are available. By comparing equations 8 and 10, one obtains $$\tilde{P}_{k,l} = \frac{1}{2M} \sum_{q=-M}^{M} \frac{\Delta\alpha}{\hat{h}_M(\rho_q)} \hat{P}_{k,q} \exp(i\pi lq/M) \quad (11)$$

$$= \frac{1}{2M} \sum_{q=-M}^{M} \frac{\Delta\alpha}{\hat{h}_M(\rho_q)} \sum_{n=-M}^{M} P_{k,n} \exp(-i\pi n/M) \exp(i\pi lq/M) \quad (12)$$

$$= \sum_{j=-M}^{M} \frac{\Delta\alpha}{2M} \sum_{q=-M}^{M} \frac{\exp(-i\pi qj/M)}{\hat{h}_M(\rho_q)} P_{k,l+j} \quad (13)$$

$$= \sum_j a_j P_{k,l+j} \quad (14)$$

with $$a_j = \frac{\Delta\alpha}{2M} \sum_{q=-M}^{M} \frac{\exp(-i\pi qj/M)}{\hat{h}_M(\rho_q)}. \quad (15)$$

Thus, for example, $$a_j = \frac{1}{2M} \left( 1 + 2 \sum_{q=1}^{M} 1 \frac{\cos(\pi qj/M)}{\mathrm{sinc}^2(0.5\pi q/M)} \right). \quad (16)$$

In the example, the following values stood for the first coefficients:

$$a_0=1.38, \quad a_1=a_{-1}=0.26, \quad a_2=a_{-2}=0.10, \quad a_3=a_{-3}=-0.05. \quad (17)$$

Due to the decreasing order of magnitude of the values of these coefficients, it is adequate to select low values for J (for example, 1, 2 or 3), the use of such lower values being advantageous for the calculating economy.

The reduction of the smoothing effect of the interpolation $h(\alpha)$, accordingly, can also be effected by a short discrete convolution in the spatial domain, constituting a second embodiment of the invention.

The short convolution can be combined with the interpolation $h(\alpha)$ to obtain $$\tilde{P}_{k,l} = \sum_{j=-J}^{J} \sum_{n=-M}^{M} a_j(\alpha_{k,l+j} - \alpha_n) F_n \quad (18)$$

$$= \sum_{n=-M}^{M} g_l(\alpha_{k,l} - \alpha_n) F_n, \quad (19)$$

as a result of which a modified interpolation rule $g(\alpha)$ arises. When the approximate values $$J=1, \quad a_0=1+w, \quad a_1=a_{-1}=-0.5 w$$

are selected in the example, then one obtains $$g(\alpha) = \begin{cases} 1+w-(1+1.5w)\dfrac{|\alpha|}{\Delta\alpha} & \text{for } |\alpha| \leq \Delta\alpha \\ \left(\dfrac{|\alpha|}{2\Delta\alpha} - 1\right) w & \text{for } \Delta\alpha < |\alpha| \leq 2\Delta\alpha \\ 0 & \text{for } 2\Delta\alpha < |\alpha|. \end{cases} \quad (20)$$

Figure 2:
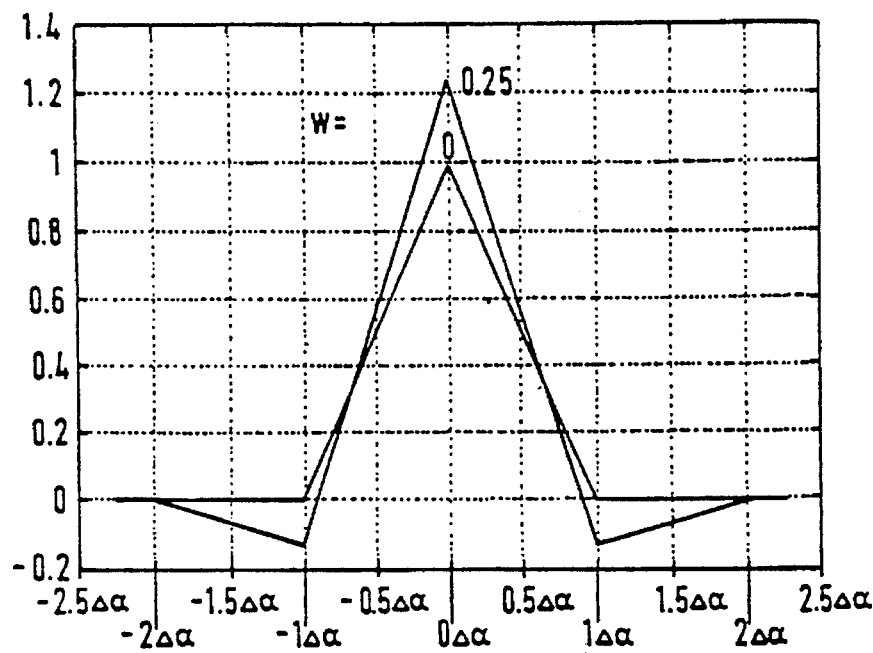
FIG. 2 is a graph of a function which arises in the interpolation of data between a first geometry, in which the measured data are obtained, and a second geometry which is used for image reconstruction.
Figure 3:
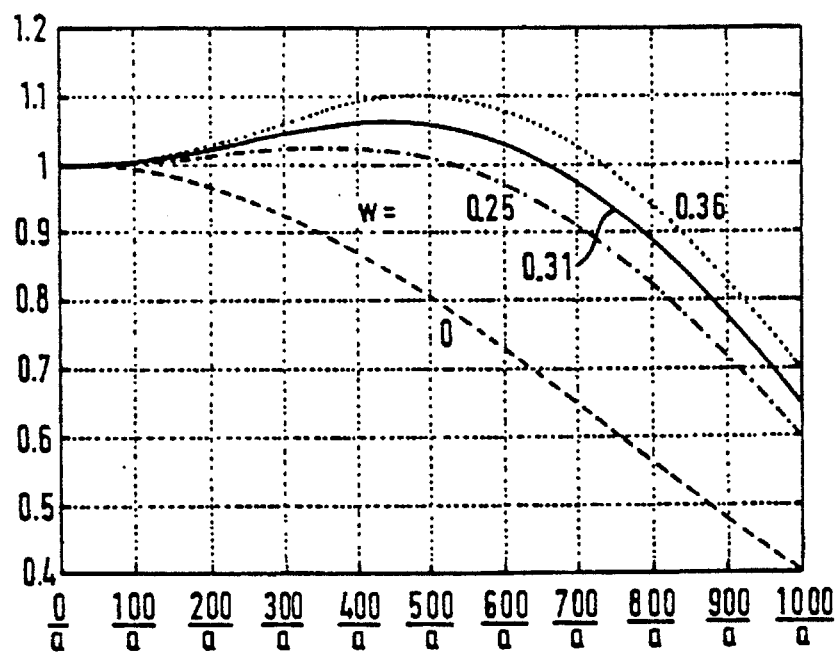
FIG. 3 shows examples of the Fourier transform of the function of FIG. 2 in accordance with the principles of the present invention.

This function $g(\alpha)$ is shown in FIG. 2 and contains the initial interpolation $h(\alpha)$ for $w=0$. FIG. 3 shows examples of the Fourier transform of the exemplary function $g(\alpha)$ for $\rho_q = 0, \ldots, 0.5/\alpha$ for various values of $w$.

The interpolation and the compensation of the smoothing in the spatial domain can be combined to form a modified interpolation.

The example of the conversion onto a shifted raster having the same sampling interval as in the case of the initial data $F_n$ with the assistance of the linear interpolation only serves the purpose of an illustrative explanation. The inventive concept is directed to a universal conversion with arbitrary interpolations.

Although modifications and changes may be suggested and though the present invention has been described with reference to a specific embodiment, those of skill in the art will recognize that changes may be made thereto without departing from the scope and spirit of the invention as set forth in the appended claims.

We claim as our invention:

1. A method for operating a computed tomography apparatus comprising the steps of:

irradiating an examination subject with an x-ray beam from a plurality of different angular positions for obtaining a measured data set in a first geometry;

reconstructing a tomographic image of said examination subject including interpolation of said measured data set in a second geometry, the interpolation of said measured data producing a smoothing of said measured data; and compensating for said smoothing of said measured data by dividing said measured data in the frequency space by an average Fourier transform employed in the interpolation of said measured data.

2. A method for operating a computed tomography apparatus comprising the steps of:

irradiating an examination subject with an x-ray beam from a plurality of different angular positions for obtaining a measured data set in a first geometry;

reconstructing a tomographic image of said examination subject including interpolation of said measured data set in a second geometry, the interpolation of said measured data producing a smoothing of said measured data; and compensating for said smoothing by conducting a discrete convolution of said measured data in the spatial domain.

3. A method for operating a computed tomography apparatus as claimed in claim 2 wherein said discrete convolution of said measured data in the spatial domain is conducted in combination with said interpolation of said measured data.

* * * * *